United States Patent
Harper

(10) Patent No.: US 12,364,519 B2
(45) Date of Patent: Jul. 22, 2025

(54) DISPENSING FASTENERS

(71) Applicant: GLOBUS MEDICAL, INC., Audubon, PA (US)

(72) Inventor: Michael Harper, Pottstown, PA (US)

(73) Assignee: Globus Medical, Inc., Audubon, PA (US)

( * ) Notice: Subject to any disclaimer, the term of this patent is extended or adjusted under 35 U.S.C. 154(b) by 328 days.

(21) Appl. No.: 17/934,325

(22) Filed: Sep. 22, 2022

(65) Prior Publication Data

US 2023/0020483 A1  Jan. 19, 2023

Related U.S. Application Data

(63) Continuation of application No. 16/734,454, filed on Jan. 6, 2020, now Pat. No. 11,484,353, which is a continuation of application No. 15/214,498, filed on Jul. 20, 2016, now Pat. No. 10,548,642, which is a continuation of application No. 13/461,159, filed on May 1, 2012, now Pat. No. 9,421,037.

(51) Int. Cl.
| | |
|---|---|
| *A61B 17/58* | (2006.01) |
| *A61B 17/56* | (2006.01) |
| *A61B 17/68* | (2006.01) |
| *A61B 17/70* | (2006.01) |
| *A61B 17/88* | (2006.01) |
| *A61B 17/068* | (2006.01) |

(52) U.S. Cl.
CPC .......... *A61B 17/7091* (2013.01); *A61B 17/58* (2013.01); *A61B 17/68* (2013.01); *A61B 17/7035* (2013.01); *A61B 17/7037* (2013.01); *A61B 17/7076* (2013.01); *A61B 17/7082* (2013.01); *A61B 17/8875* (2013.01); *A61B 17/068* (2013.01); *A61B 2017/567* (2013.01); *A61B 2017/681* (2013.01)

(58) Field of Classification Search
CPC ............ A61B 17/7091; A61B 17/7074; A61B 17/8875; A63F 11/0002
See application file for complete search history.

(56) References Cited

U.S. PATENT DOCUMENTS

| | | | |
|---|---|---|---|
| 7,967,828 B2 * | 6/2011 | Moore ............... | A61B 17/7091 |
| | | | 606/86 A |
| 9,918,755 B2 * | 3/2018 | Bootwala ........... | A61B 17/7074 |
| 2004/0243139 A1 * | 12/2004 | Lewis ............... | A61B 17/8891 |
| | | | 606/301 |
| 2005/0149031 A1 | 7/2005 | Ciccone | |

(Continued)

*Primary Examiner* — Eduardo C Robert
*Assistant Examiner* — Holly Joanna Lane

(57) ABSTRACT

A surgical instrument enables dispensing of a series of fasteners within a patient's body. The device includes a magazine sized and dimensioned to hold a series of fasteners, the series of fasteners insertable through an opening at the end of the magazine. A splined guide bore is rotatably supported within the magazine, and slidingly supports a shaft having an external surface mateable with the splined guide bore to restrict radial rotation of the shaft with respect to the support about said longitudinal axis. A biasing element is connected between the support and the shaft, to urge the shaft along a longitudinal axis towards a distal end of the instrument. A ratchet is connected to the shaft and engages the magazine to permit sliding of the shaft in a direction for dispensing fasteners only, unless disengaged with the magazine.

10 Claims, 4 Drawing Sheets

(56) References Cited

U.S. PATENT DOCUMENTS

| | | | |
|---|---|---|---|
| 2007/0276403 A1* | 11/2007 | Franks | A61B 17/7091 606/104 |
| 2008/0027466 A1* | 1/2008 | Vitali | A61B 17/122 606/143 |
| 2008/0255576 A1* | 10/2008 | Protopsaltis | A61B 17/7091 227/176.1 |
| 2009/0163962 A1* | 6/2009 | Dauster | A61B 17/7032 606/305 |
| 2010/0292710 A1* | 11/2010 | Daniel | A61B 17/0401 606/142 |
| 2010/0305625 A1* | 12/2010 | Kuntz | A61B 17/7076 606/86 R |

* cited by examiner

DISPENSING FASTENERS

CROSS-REFERENCE TO RELATED APPLICATIONS

The present application is a continuation application of U.S. patent application Ser. No. 16/734,454 filed on Jan. 6, 2020, which is a continuation application of U.S. Ser. No. 15/214,498, filed Jul. 20, 2016, which is a continuation application of U.S. Ser. No. 13/461,159, filed May 1, 2012, now issued U.S. Pat. No. 9,421,037, which are hereby incorporated by reference in their entireties.

FIELD OF THE INVENTION

The invention relates to stabilizing bones, and more particularly to securing bone screws using locking caps dispensed from a tool.

BACKGROUND OF THE INVENTION

Bones and bony structures are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column requires additional support in order to address such weaknesses. One technique for providing support is to extend a structure between adjacent bones, the structure connected at each end to a polyaxial screw "tulip", or yoke, the yoke connected to a bone screw inserted within the bone, the structure, yoke, and bone screw all rigidly mutually secured by a locking cap applied to the yoke.

SUMMARY OF THE INVENTION

In accordance with the disclosure, a device for dispensing a fastener to be implanted within a patient comprises a magazine defining a longitudinal axis and having a distal opening, the magazine sized and dimensioned to hold a series of fasteners, the series of fasteners insertable through the distal opening; a support having a splined guide bore aligned with the longitudinal axis of the magazine, the support connected to the magazine to be rotatable radially with respect to the longitudinal axis; a shaft slideably disposed within the support, the shaft having an external surface mateable with the splined guide bore to restrict radial rotation of the shaft with respect to the support about the longitudinal axis; a biasing element connected between the support and the shaft, the biasing element configured to urge the shaft along the longitudinal axis in a direction towards the distal end relative to a location of the support; and a ratchet connected to the shaft and engageable with the magazine to permit sliding of the shaft in first a direction towards the distal end, to prevent sliding of the shaft in a second direction away from the distal end in a first position, and to enable sliding of the shaft in the second direction in a second position, the ratchet movable from the first position to the second position when the support is rotated radially with respect to the longitudinal axis.

In embodiments thereof, the ratchet includes a plurality of ratchet engagement surfaces arranged along the longitudinal axis, and at least one ratchet pawl engageable with the shaft and the ratchet engagement surfaces; and, the ratchet further includes at least one cam engageable with the at least one ratchet pawl to engage and disengage the at least one ratchet pawl with the plurality of ratchet engagement surfaces.

In further embodiments thereof, one or more projections extend at the distal end, operative to block a release of an inserted fastener; one or more projections are configured to block a release of an inserted fastener when a central axis of the fastener is axially aligned with the longitudinal axis, and to release an inserted fastener when the fastener is tilted with respect to the device, whereby the central axis of the fastener is not axially aligned with the longitudinal axis; the shaft is contactable with the first inserted fastener of the series of inserted fasteners, and is thereby configured to urge the series of inserted fasteners along the longitudinal axis towards the distal end; the shaft includes first and second shaft portions in end to end contact, the at least one ratchet pawl positioned proximate a location of the end to end contact; and, the second shaft portion includes one or more guide channels configured to guide movement of the at least one ratchet pawl.

In other embodiments, the fastener is a cap for a polyaxial tulip; the device further includes one or more projections extending at the distal end, operative to block a release of an inserted cap, the one or more projections configured to engage a first portion of the cap, wherein a second portion of the cap projects from the distal end, the projecting second portion thereby being engageable with the polyaxial tulip.

In yet further embodiments, one or more apertures are formed radially about a portion of the magazine, one or more posts are connected to the support and project through the one or more apertures, and the one or more posts are moveable to radially rotate the support.

In another embodiment, a barrel surrounds a portion of the magazine, the barrel connectable to the one or more posts, the barrel rotatable to rotate the support; the ratchet includes one or more ratchet pawls, the ratchet pawls engageable with the magazine, the ratchet pawls movable in a direction transverse to the longitudinal axis; the one or more ratchet pawls are biased in a direction of engagement with the magazine; the magazine is provided with one or more apertures positioned to provide a visible indication of a number of inserted fasteners; and, the ratchet includes one or more ratchet pawls each provided with a ramped surface, the ratchet pawls thereby operative to permit sliding of the shaft in the first direction.

In another embodiment of the disclosure, a device for dispensing a fastener to be implanted within a patient comprises a magazine defining a longitudinal axis and having a distal opening, the magazine sized and dimensioned to hold a series of fasteners, the series of fasteners insertable through the distal opening, the magazine including a plurality of ratchet engagements disposed along the longitudinal axis within an interior of the magazine; a support having a splined guide bore aligned with the longitudinal axis of the magazine, the support connected to the magazine to be rotatable radially with respect to the longitudinal axis; a shaft slideably disposed within the support, the shaft having an external surface mateable with the splined guide bore to restrict radial rotation of the shaft with respect to the support about the longitudinal axis; a biasing element connected between the support and the shaft, the biasing element configured to urge the shaft along the longitudinal axis in a direction towards the distal end relative to a location of the support; and one or more ratchet pawls connected to the shaft and engageable with the plurality of ratchet engagements, and configured to permit sliding of the shaft in first a direction towards the distal end, to prevent sliding of the shaft in a second direction away from the distal end in a first position, and to enable sliding of the shaft in the second direction in a second position, the ratchet movable from the first position to the second position when the support is rotated radially with respect to the longitudinal axis.

In variations thereof, the ratchet further includes at least one cam engageable with the at least one ratchet pawl to engage and disengage the at least one ratchet pawl with the plurality of ratchet engagement surfaces; and, the device further includes one or more projections extending at the distal end, operative to block a release of an inserted fastener, the one or more projections configured to engage a first portion of the fastener, wherein a second portion of the fastener projects from the distal end, the projecting second portion thereby being connectable with an object implanted within the patient.

In a yet further embodiment of the disclosure, a device for dispensing a fastener to be implanted within a patient comprises a magazine defining a longitudinal axis and having a distal opening, the magazine sized and dimensioned to hold a series of fasteners, the series of fasteners insertable through the distal opening, the magazine including a plurality of ratchet engagements disposed along the longitudinal axis within an interior of the magazine; a support having a splined guide bore aligned with the longitudinal axis of the magazine, the support connected to the magazine to be rotatable radially with respect to the longitudinal axis; a shaft slideably disposed within the support, the shaft having an external surface mateable with the splined guide bore to restrict radial rotation of the shaft with respect to the support about the longitudinal axis; a biasing element connected between the support and the shaft, the biasing element configured to urge the shaft along the longitudinal axis in a direction towards the distal end relative to a location of the support; one or more ratchet pawls each having a sloped surface and connected to the shaft and engageable with the plurality of ratchet engagements, and configured to permit sliding of the shaft in first a direction towards the distal end, to prevent sliding of the shaft in a second direction away from the distal end in a first position, and to enable sliding of the shaft in the second direction in a second position, the ratchet movable from the first position to the second position when the support is rotated radially with respect to the longitudinal axis; and one or more ratchet pawl biasing elements configured to urge the one or more ratchet pawls in a direction of engagement with the plurality of ratchet engagements.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

Figure 1:
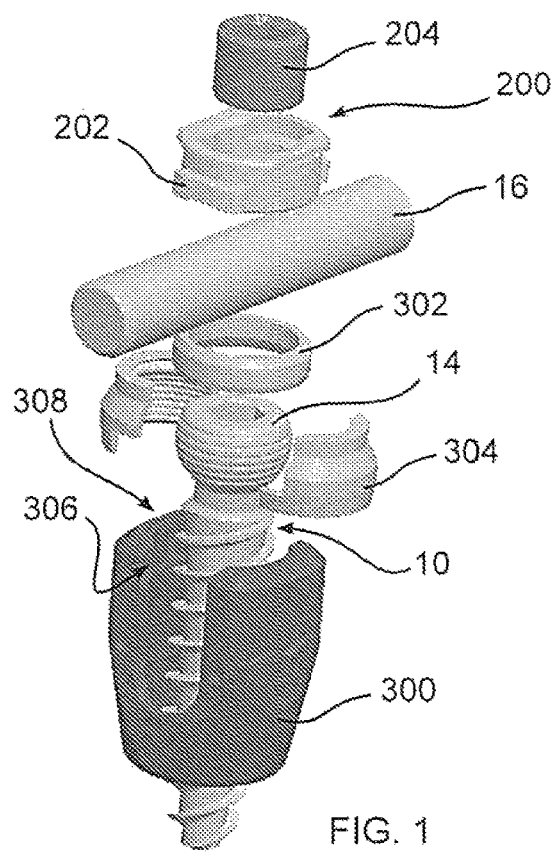
FIG. 1 is a perspective view of a spine stabilization device usable with a tool of the disclosure.

FIG. 1 illustrates an exploded view of a connecting structure extendable between bones. A bone screw 10 is passed through a yoke 300, in this example a polyaxial pedicle screw "tulip". Bone screw 10 extends from yoke 300 into bone to be stabilized (not shown), for example a vertebra. In this embodiment, bone screw 10 is provided with a polyaxial head 14, which may nest within yoke 300 at any of a wide variety of angles, enabling the medical practitioner to orient yoke 300 at a desired angle with respect to the bone. One example of screw 10 is a polyaxial pedicle screw, although other screw types may be used in combination with devices of the disclosure. A stabilizing structure, in this example rod 16, is passed into yoke 300, whereby head 14 and rod 16 lie below an upper surface 308 of yoke 300, and when so disposed, may be secured by the introduction of a fastener, or cap 200. Additional securing elements 302, 304 may be provided to improve a connection of head 14 and rod 16 within yoke 300.

In accordance with the disclosure, cap 200 is provided with one or more engagement tabs 202 which cooperate with mating grooves 306 within yoke 300, to prevent separation of cap 200 from yoke 300, once tabs 202 and grooves 306 are engaged. It should be understood that, alternatively or additionally, mating grooves 306 may be provided within cap 200, and tabs 202 may be provided within yoke 300. A set screw 204 threadably passes through cap 200, and may be rotated to increase a pressure between cap 200, head 14, and rod 16, to rigidly secure the assembly, thereby rigidly connecting rod 16 to a bone.

When rod 16 is thus secured to another bone with a similar assembly, the two bones so connected are stabilized with respect to each other. Such stabilization is effective, for example, in the spine, connecting vertebrae; however, any bones of the body, and any number of bones, may be stabilized in this manner. Rod 16 may be constructed to be rigid or resilient, enabling a desired amount of flex between stabilized bones.

In accordance with the disclosure, a plurality of caps 200 are individually discharged or dispensed from a single instrument or tool 100. In accordance with one embodiment, for example, eight caps 200 may be dispensed. While a threaded cap may be dispensed using tool 100, a non-threaded cap 200 as shown and described herein is advantageously dispensed, as such caps do not have the risk of cross threading, or accidental disengagement, in the manner that threaded caps do, and are more quickly installed.

It should be understood that a fastener, or cap 200, may be attached to other implants or structures as currently known, or hereinafter developed. Moreover, cap 200 may have other forms than those illustrated in the accompanying drawings. For example, they may be threaded, or may engage a yoke, nut, or other embedded structure in a different way, for example by using a snap-fit, or interference fit, while advantageously being dispensed and installed using tool 100 of the disclosure.

Figure 2:
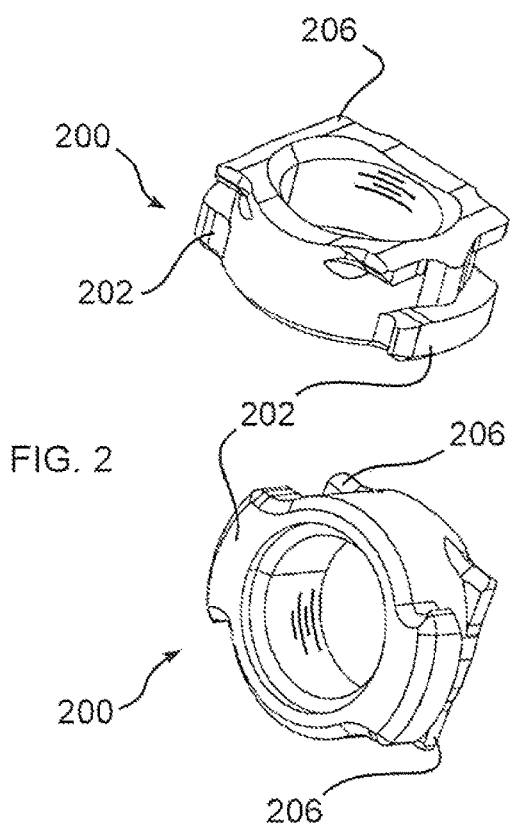
FIGS. 2 and 3 are perspective views of a locking cap in accordance with the disclosure.
Figure 3:
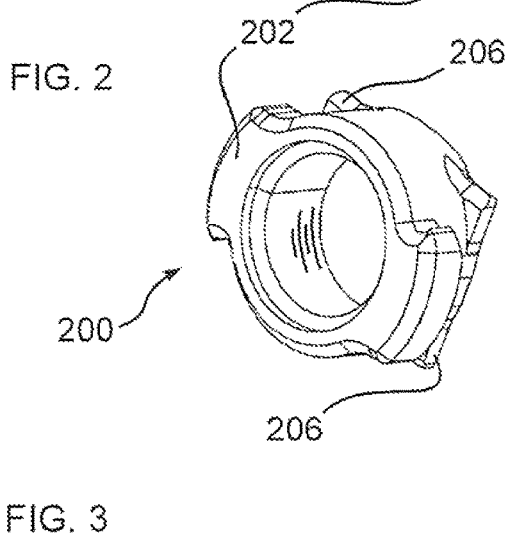

In accordance with the disclosure, caps 200 are dispensed by a tool 100. In the embodiment of FIGS. 2-3, cap 200 further includes tool flange 206, sized and dimensioned to engage mating portions of tool 100, as described further, below. While cap 200 of FIGS. 2-3 is illustrative of a cap adapted to matingly engage tool 100, as described further herein, it should be understood that tool 100 may be adapted to engage other cap designs, including the cap illustrated in FIG. 1.

Figure 4:
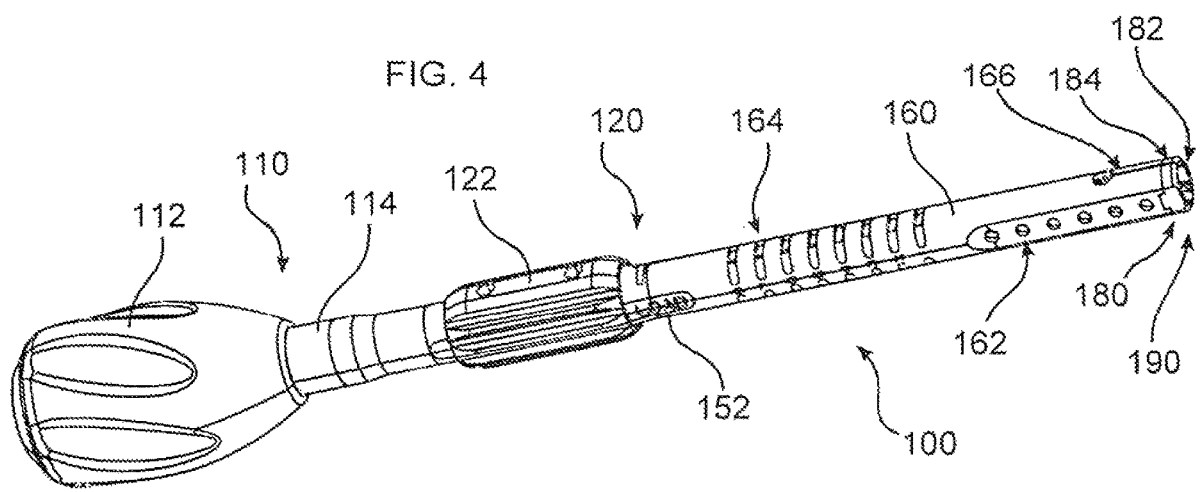
FIG. 4 is a perspective view of a dispensing tool of the disclosure.

In FIG. 4, an embodiment of tool 100 in accordance with the disclosure includes a handle assembly 110, a latch assembly 120 including a release knob, or latch barrel 122, a loading tube, or magazine 160, and a retention tip 180. Handle assembly 110 includes a grip 112, and a handle extension 114 and handle adapter 114A. Caps 200 are loaded into magazine 160 by being inserted into retention tip 180, each successive cap pushing the previously loaded caps further into magazine 160. Caps 200 may be arranged, for example, in a tray that orients caps 200 correctly for insertion. Apertures 162 within magazine 160 provide a visible indication of loaded caps 200, advantageously indicated by a difference in color between an exterior surface of magazine 160 and caps 200.

When magazine 160 is loaded with caps 200, tabs 202 of the last loaded cap 200 project beyond tip 180, whereby tabs 202 may be engaged with yoke 300. Once thus engaged, tool 100 may be tilted to change an orientation between tip 180 and cap 200, secured to yoke 300, thereby enabling passage of cap 200, and particularly to admit passage of tool flange 206 past a mating flange engagement 182 of tip 180, releasing a cap 200 from magazine 160 and tool 100.

Figure 5:
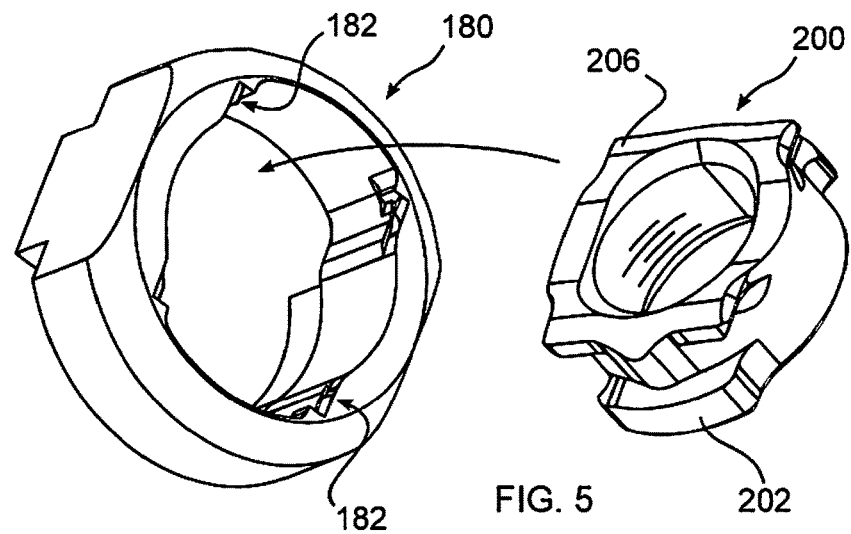
FIG. 5 is an enlarged perspective view illustrating mating portions of a tool tip and a cap, in accordance with the disclosure.

FIG. 5 illustrates a mating engagement between tool flange 206 and flange engagement 182. In this embodiment, flange engagement 182 forms an interference fit with one or more portions of tool flange 206. As explained further below, cap 200 is resiliently urged against tip 180, thereby pressing tool flange 206 of cap 200 against flange engagement 182 of tip 180, preventing passage of cap 200 out of tool 100. Once a longitudinal axis of tool 100 is tilted with respect to a central bore axis of cap, portions of tool flange 206 may pass portions of flange engagement 182, thereby releasing cap 200. Until tool 100 is tilted while dispensing a cap 200 connected to yoke 300, caps 200 are maintained coaxially aligned with a longitudinal axis of tool 100 by a mating shape and dimension of in interior of magazine 160 and an exterior shape and dimension of cap 200, together with a biasing force provided by biasing member 136.

In another embodiment, tip 180 and or portions of magazine 160 are resilient, and may bend to admit passage, or facilitate passage, of cap 200 past flange engagement 182. For example, flange engagement 182 may comprise resilient extensions. Alternatively, as shown in FIG. 4, tip 180 or magazine 160 may be provided with reliefs 166, 184, to facilitate sufficient expansion of tip 180 or magazine 160 to enable passage of a cap 200 from tool 100.

Figure 6:
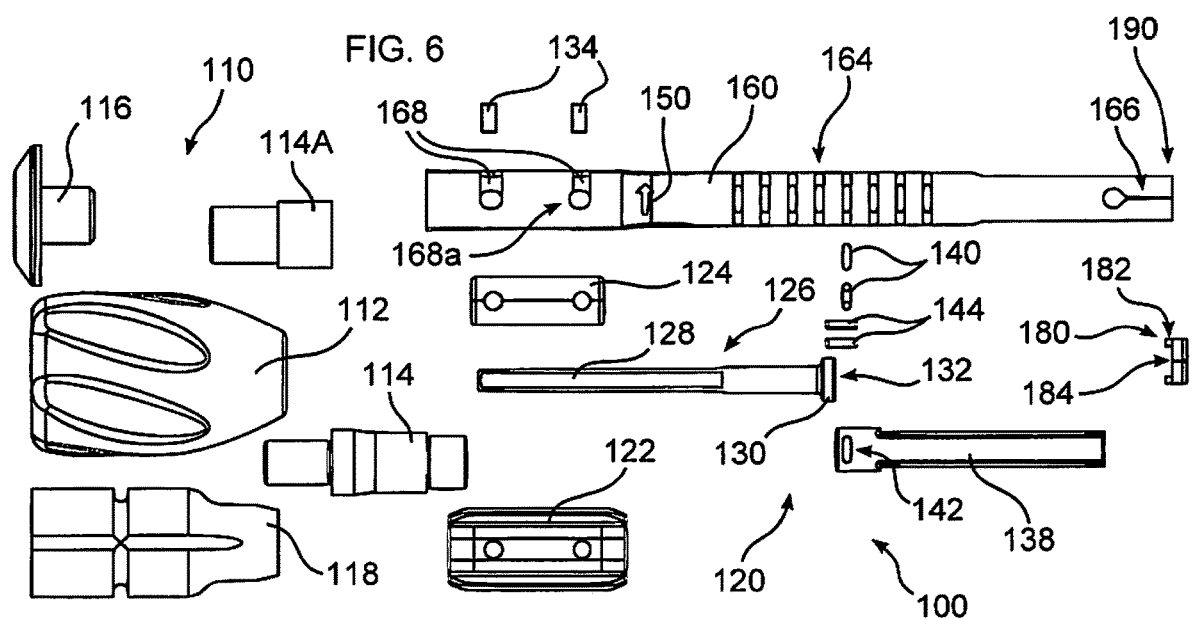
FIG. 6 is an exploded side view of parts of the tool of FIG. 4.
Figure 7:
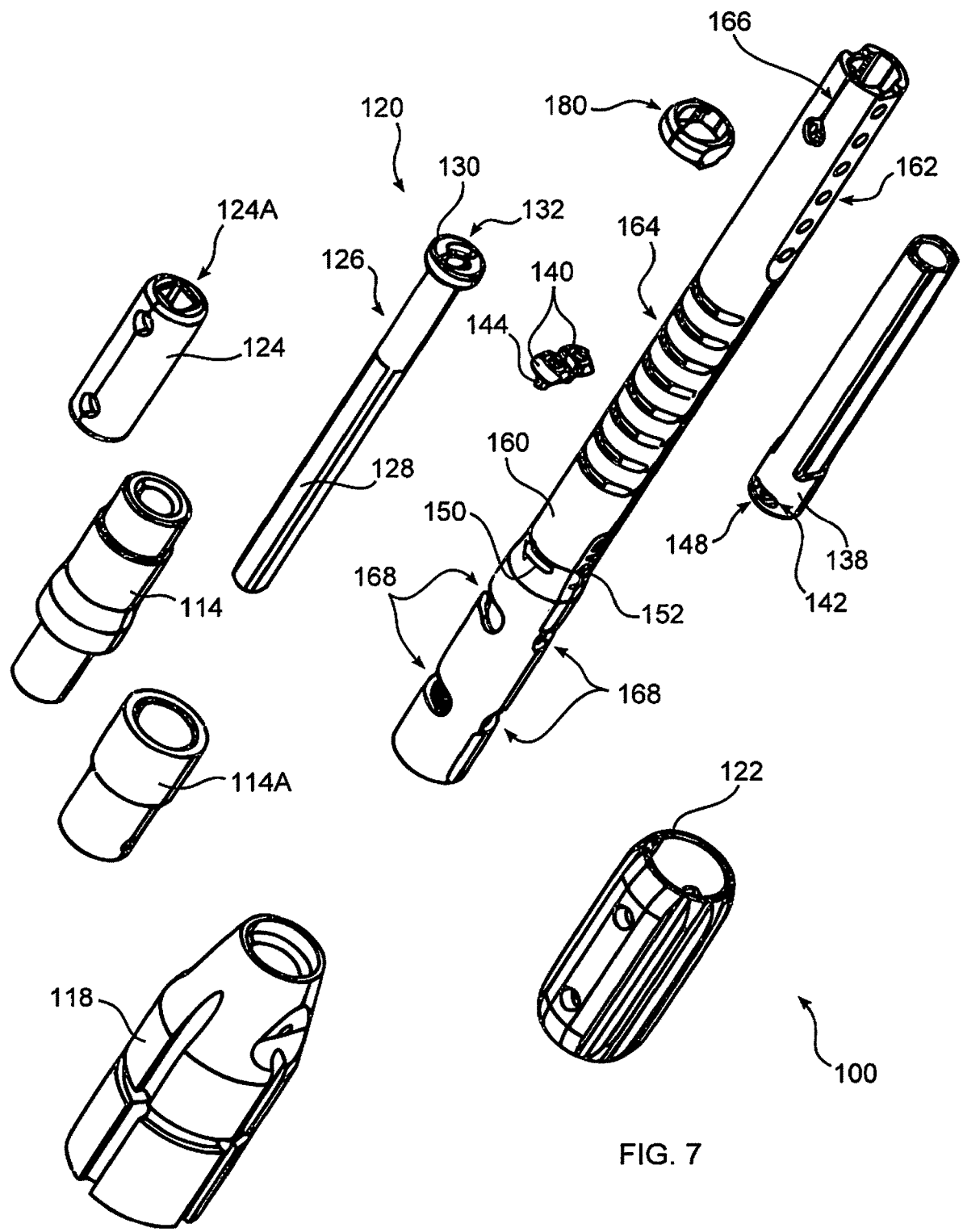
FIG. 7 is an exploded perspective view of parts of the tool of FIG. 4.
Figure 8:
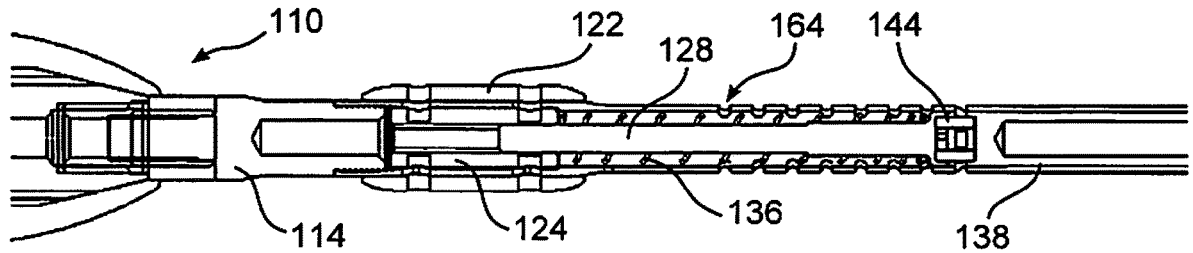
FIG. 8 is a cross-section of the tool of FIG. 4, taken through a longitudinal center of the tool.

FIG. 6 is an exploded view of tool 100, the parts arranged, for ease of understanding, in an original axial displacement along a longitudinal axis of tool 100, but displaced radially, with internal portions positioned externally. FIGS. 7 and 8 may additionally be referenced with respect to the following discussion. Additionally illustrated are cover 116, handle core 118, handle extension 114, and handle adapter 114A. Portions of handle assembly 110 having reference numerals 100 to 120 are mutually connected to not rotate with respect to each other. While handle assembly 110 comprises a plurality of parts, for example for ease of manufacture, it should be understood that a single part may be used. Grip 112 is advantageously formed with a resilient material, to promote a secure manual grip, and for comfort.

Handle extension 114 of handle assembly 110 is non-rotatably connected to magazine 160, whereby rotation of handle assembly 110 causes rotation of magazine 160. Rotatably mounted within magazine 160 are cam actuator shaft support 124 and cam actuator 126, the latter including cam actuator shaft 128, cam head 130, and cam surfaces 132 (shown in FIG. 9). Cam actuator shaft 128 is slidingly received within a guiding splined bore 124A (visible in FIG. 7) of shaft support 124, whereby shaft support 124 and actuator shaft 128 rotate in unison about a common longitudinal axis, while actuator shaft 128 is slideable axially along the common longitudinal axis. While the illustrated embodiment of splined bore 128A has a square shape, corresponding to an external shape of cam actuator shaft 128, other mateable shapes may be employed.

Latch barrel 122 is rotatably mounted about an exterior surface of magazine 160. One or more latch posts 134 pass through a portion of latch barrel 122, through one or more cutout portions 168 of magazine 160, and into shaft support 124, whereby rotation of latch barrel 122 causes rotation of shaft support 124 within magazine 160. Cutout portions 168 are oriented radially about a longitudinal axis of tool 100, and define an arc through which latch posts 134 may travel, thereby limiting a rotational extent of latch barrel 122 and shaft support 124. Cutout portions 168 may be provided with a relief portion 168a extending along a longitudinal axis of tool 100, whereby latch barrel 122, latch posts 134, and shaft support 124 may be moved axially with respect to a longitudinal axis of tool 100, to maintain a rotational position of the foregoing parts against a biasing force. Latch barrel 122 is advantageously knurled or textured to ease manipulation thereof.

Cam actuator 126 is urged towards a distal end 190 of tool 100, in a direction towards tip 180, by a biasing element 136 (shown in FIGS. 8 and 10), for example a spring, causing cam actuator shaft 128 to slide along in an axial direction along a longitudinal dimension of tool 100, within shaft support 124. Cam head 130 thus bears against a pressure transferring bar or tube, in the illustrated embodiment push rod 138, the latter bearing against any loaded caps 200. As such, caps 120 are urged towards the distal end 190 of tool 100, where they may be sequentially dispensed. Once a cap is dispensed, it is advantageously at least provisionally tightened to ensure it remains in connection with yoke 300 until the therapeutic medical procedure is complete. While push rod 138 is provided, it should be understood that actuator shaft 128 may be provided with sufficient length to drive caps 200 directly.

In order to use tool 100 to push engagement tabs 202 into yoke 300, and to thereafter turn cap 200 to lock engagement tabs 202 into grooves 306, it is advantageous to prevent movement of the cap 200 backwards, further into magazine 160. To accomplish this, one or more ratchet pawls 140 pass through ratchet guides 142 disposed within an end of push rod 138, and thence into engagement with ratchet engagements 164 of magazine 160. In this manner, push rod 138 is axially and radially fixed with respect to magazine 160, and handle assembly 110. While ratchet engagements 164 are illustrated as openings in magazine 160, they may be formed as ledges, ridges, or other shaped surfaces which are sufficient to engage and support ratchet pawls 140, but which do not necessarily pass through magazine 160. When ratchet engagements 164 form apertures, these may serve as an additional indicator of caps 200 loaded, or remaining, facilitated, for example, if ends of ratchet pawls 140 are provided with a color which contrasts with a color of an exterior surface of magazine 160.

Ratchet pawls 140 are advantageously formed with ramped surfaces 140A, whereby when a cap 200 is released, ratchet pawls 140 advance upon ramped surface 140A through a bias force exerted by biasing element 136, and are thereby released from engagement with ratchet engagement 164. Accordingly, the remaining series of caps 200 may advance towards the distal end of tool 100, until the next successive cap 200 is held by flange engagements 182. Absent ramped surfaces 140A, latching barrel 122 could be rotated to disengage ratchet pawls 140 to allow advancement of inserted caps 200. In this manner, fasteners may be dispensed, even if ratchet pawls 140 are engaged with ratchet engagements 164, but fasteners may not driven in a direction away from the distal end 190 of tool 100 unless ratchet pawls 140 are disengaged from ratchet engagements 164. Accordingly, tool 100 may be used to push caps 200 into yoke 300 against a resisting force. Tool 100 may also be used to rotate a cap 200 within a yoke 300 against a force resistant to rotation, due to a mating engagement of an outer surface of cap 200 with an interior surface of magazine 160.

Figure 9:
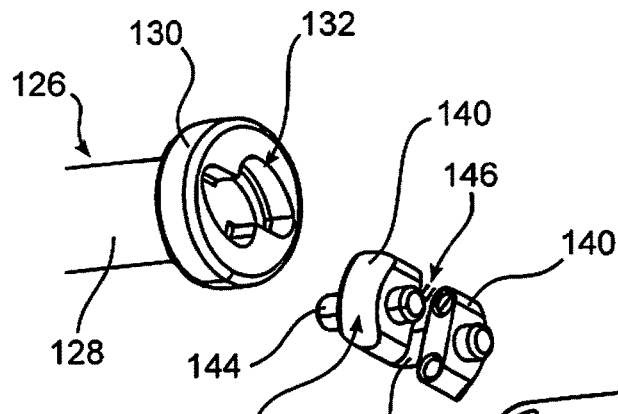
FIG. 9 is an enlarged perspective view of the cam configuration of the tool of FIG. 4.

With further reference to FIG. 9, once a cap 200 has been dispensed, ratchet pawls 140 are withdrawn from ratchet engagements 164, whereby cam actuator 126 and biasing element 136 may urge push rod 138 towards proximal end 190, to thereby position the next successive cap 200 for dispensing. To withdraw ratchet pawls 140, one or more cam surfaces 132, within cam head 130, are rotated to guide one or more ratchet pins 144, each connected to a ratchet pawl 140. The profile of each of the one or more cam surfaces 132 causes ratchet post 144 to move radially inwardly, in cooperation with cam post guide 148 within an end of push rod 138, with respect to a longitudinal axis of tool 100, thereby withdrawing ratchet pawl 140 from ratchet engagement 164 of magazine 160. A ratchet biasing element 146 is advantageously provided to urge ratchet pawl 140 radially outwards, to maintain ratchet pawl 140 in engagement with ratchet engagements 164 until cam surfaces 132 are activated, and to return latch barrel 122 to a non-actuated position. It should be understood that ratchet pawls 140 may extend through ratchet guides 142, or ratchet pawls 140 may be positioned outside of push rod 138.

To activate cam surfaces 132, cam actuator 126 is rotated by radially rotating latch barrel 122 with respect to a longitudinal axis of tool 100, to move posts 134, to thereby cause a rotation of shaft support 124. Accordingly, actuator shaft 128 rotates, turning cam head 130, and cam surfaces 132. Ratchet pins 144 are further guided to move radially inwards by passing through cam post guide 148. Rotation of latch barrel 122 may be limited by either or both of a length of cutout portions 168, or a length of a profile of cam surface 132. To facilitate disassembly of tool 100, for example for repair or cleaning, latch barrel may be maintained in a rotated or actuated position, while push rod 138 is fully removed following dispensing of the last loaded cap 200. Latch posts 134 may be removed, for example by unthreading them from shaft support 124, to release the remaining moveable parts from magazine 140. Tool 100 may be cleaned in an assembled or an unassembled state, for example using an autoclave or gas sterilization.

In accordance with an embodiment of the disclosure, to use tool 100, latch barrel 122 is rotated to an extent of rotation according to a design of cam surface 132 sufficient to disengage or withdraw ratchet pawls 140, for example 90 degrees. Rotation is along a direction indicated by an arrow indicia 150, until a mark upon latch barrel 122 is aligned with indicia 150 ("Load") on magazine 160. In this configuration, tip 180 is pushed against a cap 200 until the cap enters magazine 160, the cap typically resiliently held in place within a tray. Once all caps 200 are loaded, latch barrel 122 is rotated away from the "Load" position, to a "Use" position (not shown) which may also be provided as indicia upon a surface of tool 100, to thereby release ratchet pawls 140 to reengage magazine 140. Next, a projecting portion of cap 200 is inserted into a yoke 300, and rotated, for example 30 degrees, to engage yoke 300. After such engagement, tool 100 is tilted to free the engaged cap 200 from engagement with one or more projections, or mating flange engagements 182 of tip 180, to release cap 200 from tool 100. Following such disengagement, the next loaded cap 200 advances due to a force imparted by biasing element 136, and the inserted cap 200 may be tensioned within yoke 300. The newly projecting cap 200 is inserted into another yoke 300, and the process is repeated from that point until all loaded caps 200 are dispensed and inserted within their respective yokes 300.

Figure 10:
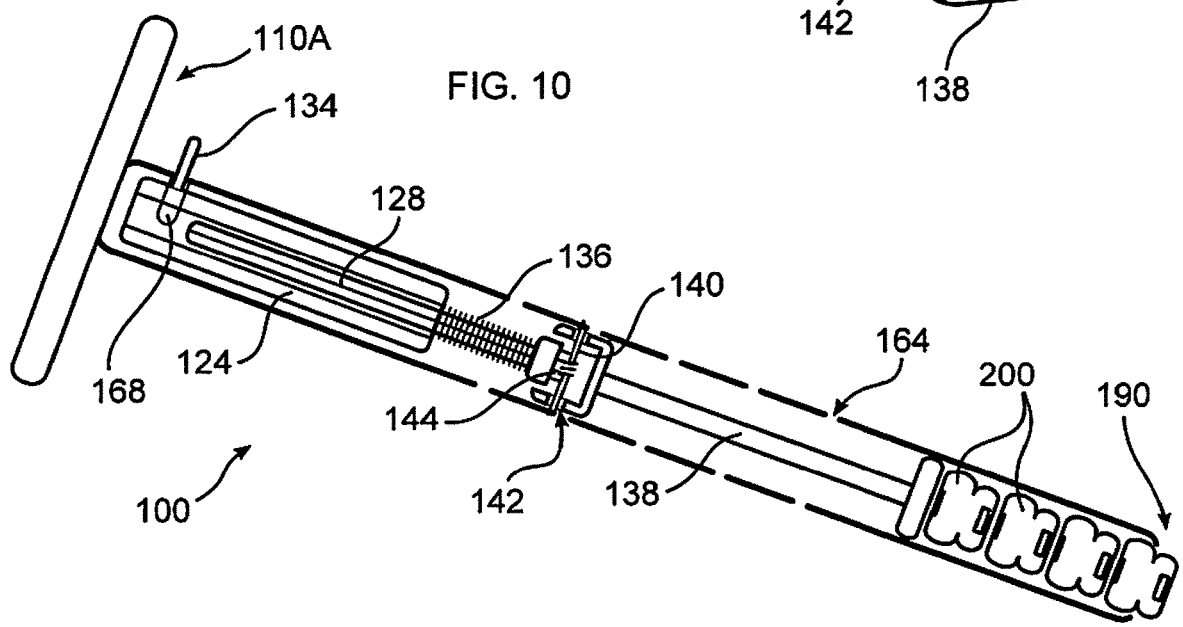
FIG. 10 is a cross-section of an alternative tool of the disclosure, taken through a longitudinal center of the tool.

FIG. 10 illustrates an alternative embodiment of a tool in accordance with the disclosure, wherein handle assembly 110A includes a t-handle, and latch post 134 is directly manipulable. While biasing element 136 is illustrated as a compression spring, it should be understood that other forms of biasing may be provided, including a torsion spring, volute spring, and compressed gas bladder. While magazine 140 of FIG. 10 is configured to hold five caps 200, it should be understood that any number of caps 200 may be dispensed, depending on the height of caps 200, and a length of magazine 140.

Tool 100 may be fabricated using any known materials which are advantageously biocompatible, including for example PEEK (polyether ether ketone), ultra high molecular weight polyethylene (UHMW), titanium, stainless steel, or a cobalt chromium alloy. Other polymers, metals, alloys, or composite materials may alternatively be used, as known in the art, or hereinafter developed. One or more portions of tool 100 may be formed by extrusion, milling, forging, casting, molding, or any other method advantageously used for the materials selected and the structure intended.

The tool and method of the disclosure enables increased efficiency and reduced error in applying caps for securing screws. More particularly, caps 200 may be inserted more quickly than other known methods of insertion, for example by manual installation or installation using a tool which accommodates a single cap 200. Insertion speed is important, because it reduces the time a patient undergoes anesthesia, reducing tissue damage by reducing time during which tissue is retracted or manipulated, and reduces cost by reducing staff and operating room use time.

All references cited herein are expressly incorporated by reference in their entirety. There are many different features to the present invention and it is contemplated that these features may be used together or separately. Unless mention was made above to the contrary, it should be noted that all of the accompanying drawings are not to scale. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A method for dispensing a series of fasteners into one or more screw members, the method comprising:
   providing the one or more screw members configured to be inserted into one or more bone members;
   providing a rod that extends between the one or more screw members; and
   providing a device for dispensing a series of fasteners in the one or more screw members, wherein the device comprises:
      a handle assembly;
      a magazine defining a longitudinal axis and having a distal opening, wherein the magazine is sized and configured to hold a series of fasteners, the series of fasteners insertable through said distal opening; and
      a retention tip
      wherein the device further comprises a cam actuator and a biasing element, wherein the device further comprises one or more ratchet pawls that extend through ratchet guides disposed within an end of a push rod and wherein the one or more ratchet pawls include ramped surfaces,
      wherein the device further comprises a support having a splined guide bore aligned with said longitudinal axis of said magazine, said support connected to said magazine to be rotatable with respect to said longitudinal axis,
      wherein the device further comprises a shaft slideably disposed within said support, and
      wherein the device further comprises a biasing element connecting between said support and said shaft, said biasing element configured to urge said shaft along said longitudinal axis in a direction towards said distal opening relative to a location of said support;
   dispensing the series of fasteners in to the one or more screw members.

2. The method of claim 1, wherein the series of fasteners comprise one or more locking caps.

3. The method of claim 2, wherein the one or more locking caps comprise a tab and a tool flange.

4. The method of claim 3, wherein the one or more locking caps comprise a pair of tabs and a pair of tool flanges.

5. The method of claim 1, wherein the retention tip is resilient.

6. The method of claim 1, wherein the device further comprises a series of fasteners received in the device, wherein the series of fasteners comprise at least one tab and at least one flange above the at least one tab.

7. The method of claim 6, wherein the series of fasteners comprise one or more locking caps.

8. The method of claim 7, wherein the one or more locking caps comprise a pair of tabs.

9. The method of claim 7, wherein the one or more locking caps comprise a pair of flanges.

10. The method of claim 7, wherein the retention tip is resilient.

* * * * *